United States Patent [19]

Kamishita et al.

[11] 4,244,942

[45] Jan. 13, 1981

[54] CREAMY PREPARATION CONTAINING STEROID AND PROCESS FOR THE PREPARATION THEREOF

[75] Inventors: Takuzo Kamishita; Kazuhiko Kamishita, both of Takatsuki, Japan

[73] Assignee: Toko Yakuhin Kogyo Kabushiki Kaisha, Ooyodo, Japan

[21] Appl. No.: 46,931

[22] Filed: Jun. 8, 1979

[30] Foreign Application Priority Data

Mar. 7, 1978 [JP] Japan ................................. 53-26314

[51] Int. Cl.³ ...................... A61K 31/78; A61K 31/56
[52] U.S. Cl. ........................................ 424/81; 424/243
[58] Field of Search .................................. 424/243, 81

[56] References Cited

U.S. PATENT DOCUMENTS

| 4,008,321 | 2/1977 | Kamishita et al. | 424/243 |
| 4,017,615 | 4/1977 | Shastri et al. | 424/243 |

Primary Examiner—Elbert L. Roberts
Attorney, Agent, or Firm—Stevens, Davis, Miller & Mosher

[57] ABSTRACT

A creamy preparation containing a steroid compound having a pH of 4 to 7 and a viscosity of 10,000 to 100,000 centipoises, which is applicable to the skin and comprises a steroid compound (corticosteroids), a fluid oily substance, a nonionic surfactant, and an aqueous solution of carboxyvinyl polymer, said preparation having been neutralized with a basic substance, and a process for the preparation thereof. The creamy preparation has an excellent absorbability of the active steroid, excellent stability and excellent spreadability onto the skin and also good feeling in use.

5 Claims, No Drawings

CREAMY PREPARATION CONTAINING STEROID AND PROCESS FOR THE PREPARATION THEREOF

The present invention relates to a novel creamy preparation containing a steroid compound which is applicable to skin. More particularly, it relates to a creamy preparation having a pH of 4 to 7 and a viscosity of 10,000 to 100,000 centipoises at 20° C. which is prepared by dissolving a steroid compound in crotamiton and/or propylene glycol, adding to the solution a fluid oily substance, a nonionic surfactant and an aqueous solution of a carboxyvinyl polymer, and adding with stirring thereto a water-soluble basic substance.

It is well known that some steroid compounds such as prednisolone, dexamethasone, cortisone, etc. have excellent antiinflammatory activities and are usually used as an antiinflammatory agent in the form of an ointment. However, ointments feel sticky and unpleasant when applied to the skin, and further, due to insufficient contact of the steroid with the skin, the steroid is insufficiently absorbed from the skin. Moreover, the applied surface is rubbed with clothes, which results in loss of the active ingredient and also soiling of clothes. Besides, at a high temperature of 40° C. or higher, ointments are liable to become unstable.

In order to overcome the drawbacks of ointment, the present inventors have provided a transparent, gelatinous preparation which is prepared by mixing a solution of a steroid compound in crotamiton with propylene glycol and adding the resulting mixture to an aqueous solution of a carboxyvinyl polymer and finally adding an organic amine to the resulting mixture (cf. U.S. Pat. No. 4,008,321).

As a result of a further studying by the present inventors, there has been found a creamy preparation of a steroid compound which has greater stability and excellent feeling in use.

The present invention provides a novel creamy preparation of a steroid compound having a pH of 4 to 7 and a viscosity of 10,000 to 100,000 centipoises at 20° C., which is prepared by dissolving a steroid compound in crotamiton and/or propylen glycol, adding thereto a fluid oily substance, a nonionic surfactant and an aqueous solution of a carboxyvinyl polymer, and adding with stirring thereto a water-soluble basic substance while heating the mixture at about 70° to 80° C.

The steroids to be contained in the present cream preparation include corticosteroids and esters thereof, such as prednisolone, cortisone, triamcinolone, betamethasone, hydrocortisone, dexamethasone, methylprednisolone, fluocinolone, fluorometholone, triamcinolone acetonide, fluocinolone acetonide, fluocinonide, clobetasol 17-propionate, dexamethasone valerate, betamethasone valerate, betamethasone acetate, betamethasone benzoate, flumethasone, prednisolone acetate, hydrocortisone valerate, betamethasone propionate, bechlometbasone dipropionate, or the like. The steroid compounds are incorporated into the present creamy preparation in an effective amount which varies depending on the kinds of the steroids, but is usually in a range of 0.001 to 1% by weight based on the total weight of the preparation.

These steroids are usually insoluble in water, but are easily soluble in crotamiton (i.e. N-crotonyl-N-ethyl-o-toluidine). In the present invention, the steroids are firstly dissolved in crotamiton or propylene mglycol or a mixture thereof. The steroids are dissolved more in crotamiton than in propylene glycol. Although crotamiton can be used alone, it is not preferable to include the crotamiton of 10% by weight or more in the present creamy preparation. Besides, propylene glycol may also be used alone, but because of less solubility of steroids in propylene glycol, it is usually used only when the steroid compound has a comparatively high solubility in propylene glycol, for instance, in case of dexamethasone.

Accordingly, it is preferable to use a mixture of crotamiton and propylene glycol. Dissolution of a steroid compound in a mixture of crotamiton and propylene glycol may be carried out by firstly dissorbing the steroid compound in either one of crotamiton and propylene glycol and adding another one to the solution. To use the mixture of crotamiton and propylene glycol is preferable also from the viewpoint that it can give an excellent emulsion stability and spreadability to the preparation. When propylene glycol is used in a too large amount, the preparation has undesirable irritation to the skin, and hence, it should be used in an amount of less than 20% by weight. From the standpoint of solubility of steroids in the solvent, prevention of crystallization of steroids in the preparation, and further emulsion stability, spreadability and feeling of the preparation, crotamiton is usually used in an amount of not more than 10% by weight, usually 0.5 to 10% by weight, preferably 2 to 10% by weight, and propylene glycol is usually used in an amount of less than 20% by weight, i.e. from 2 to less than 20% by weight, preferably 5 to 10% by weight, based upon the total weight of the preparation.

Fluid oily substance to be incorporated into the present creamy preparation includes higher fatty alcohols, higher fatty acids and higher fatty acid esters, oily hydrocarbons, and a mixture thereof. Suitable examples of the fluid oily substance are fatty alcohols having 8 to 18 carbon atoms, such as octyl alcohol, capryl alcohol, nonyl alcohol, lauryl alcohol, myristyl alcohol, cetyl alcohol, or stearyl alcohol; monovalent or divalent fatty acids having 8 to 18 carbon atoms, such as lauric acid, myristic acid, palmitic acid, oleic acid, linoleic acid, sebacic acid, or stearic acid; alkyl esters of the fatty acids as mentioned above wherein the alkyl moiety has 1 to 18 carbon atoms, such as isopropyl myristate, diethyl sebacate, dibutyl sebacate, dioctyl sebacate, and a mixture thereof.

The carboxyvinyl polymer is a hydrophilic vinyl polymer with active carboxyl groups which is prepared by polymerization of monomers comprising predominantly acrylic acid [cf. Chem. & Eng. News, Vol. 36, page 64 (Sept. 29, 1958)]. All commercially available carboxyvinyl polymers can be used in the present invention. Suitable examples are Carbopol 934, Carbopol 940 and Carbopol 941, which are tradenames of the products of Goodrich Chemical. The carboxyvinyl polymer has free carboxyl groups and the aqueous solution is acidic. When the carboxyvinyl polymer is neutralized with a basic substance, a sticky gel is formed.

The basic substance to be used for neutralization of carboxyvinyl polymer includes organic amines, such as an alkylamine having 1 to 4 carbon atoms (e.g. methylamine, ethylamine, or propylamine), a dialkylamine having 1 to 4 carbon atoms in each alkyl moiety (e.g. dimethylamine, diethylamine, or dipropylamine), a trialkylamine having 1 to 4 carbon atoms in each alkyl moiety (e.g. trimethylamine, triethylamine, or tripropylamine), an alkanolamine having 1 to 4 carbon atoms in the alkanol moiety (e.g. methanolamine, ethanolamine, or propanolamine), a dialkanolamine having 1 to 4 carbon atoms in each alkanol moiety (e.g. dimethanolamine, diethanolamine, dipropanolamine, or dibutanolamine), a trialkanolamine having 1 to 4 carbon atoms in each alkanol moiety (e.g. trimethanolamine, triethanolamine, tripropanolamine, or tributanolamine), and trimethylolaminomethane, and also includes inorganic bases such as ammonia, an aqueous solution of alkali metal hydroxides (e.g. sodium hydroxide, potassium hydroxide). All these basic substances can give a gel having a similar viscosity when the aqueous solution of carboxyvinyl polymer is neutralized with the basic substances.

The nonionic surfactant to be incorporated into the present creamy preparation includes sorbitan sesquioleate, sorbitan trioleate, sorbitan monooleate, sorbitan monostearate, sorbitan monolaurate, polyethylene glycol monostearate, polyoxyethylene sorbitan monooleate, polyoxyethylene sorbitan monolaurate, polyoxyethylene nonylphenyl ether, polyoxyethylene cetyl ether, polyoxyethylene lauryl ether, or a mixture thereof.

The creamy preparation of the present invention can be prepared in the following manner.

A steroid compound is firstly dissolved in crotamiton or polyethylene glycol or a mixture thereof (mixed ratio of crotamiton:polyethylene glycol, 1:10 to 5:1 by weight). To the solution are added a fluid oily substance, a nonionic surfactant and an aqueous solution of carboxyvinyl polymer, and thereto is added with stirring a water-soluble basic substance, by which the carboxyvinyl polymer is neutralized to give a viscous gel. The above step, i.e. the dissolution of the steroid compound in the solvent and the mixing the ingredients may be carried out at room temperature but are preferably carried out at about 70° to 80° C.

According to the action of the nonionic surfactant, the oily phase of the mixture of a steroid compound and a fluid oily substance and the aqueous phase of the carboxyvinyl polymer solution are uniformly mixed to give the desired creamy preparation. The creamy preparation thus obtained has a pH of 4 to 7, preferably 4 to 5.5 and a viscosity of 10,000 to 100,000 centipoises, preferably 30,000 to 80,000 centipoises, at 20° C. The creamy preparation contains 0.1 to 3.0% by weight, preferably 0.5 to 1.2% by weight, of the carboxyvinyl polymer based upon the total weight of the preparation. The carboxyvinyl polymer is usually used in the form of a 1 to 10% aqueous solution, preferably 2 to 4% aqueous solution, and after mixing the aqueous solution of carboxyvinyl polymer with the mixture of a steroid compound and other ingredients, the content of the carboxyvinyl polymer in the creamy preparation is regulated in the above range by adding thereto water.

The pH of the preparation is regulated within 4 to 7 by controlling the amount of the basic substance. When the pH value is higher than 7, i.e. in alkaline side, the preparation is unstable, and on the other hand, it is lower than 4, the preparation becomes too acidic and irritative to skin and further too large amount of carboxycinyl polymer is undesirably required for increasing the viscosity thereof.

The fluid oily substance is usually used in an amount of 5 to 50% by weight, preferably 10 to 20% by weight, based upon the total weight of the preparation, but when crotamiton, which is also an oily substance, is used in a large amount, the fluid oily substance is used in a less amount. The nonionic surfactant is used in an amount of 0.5 to 5% by weight, preferably 1 to 2% by weight, based upon the total weight of the preparation.

The creamy preparation of the present invention is a uniform white cream and the viscosity thereof does almost not vary at a high temperature (e.g. 40° C.) and at a low temperature (e.g. 0° C.) and also even when the preparation is kept for a long period of time. Moreover, even when the preparation is kept at a low temperature for a long period of time, no crystallization of the steroid compound appears. Accordingly, the present creamy preparation is very stable and does not have such drawbacks as seen in the conventional ointments, such as melting or liquefaction at summer time and hardening or solidification at winter time and also separation of the oily phase and aqueous phase.

When the creamy preparation of the present invention is applied to skin, it is contacted with salts such as sodium chloride which are contained in a very small amount in the perspiration or are present on the surface of the skin and thereby the viscosity of the preparation is rapidly decreased, and the preparation is liquefied and shows excellent spreadability onto the skin. As the result, a film of carboxyvinyl polymer is formed on the skin, which promotes the absorption of the active ingredient (steroid compound) into skin. Moreover, the film of carboxyvinyl polymer thus formed is readily dried when contacted with air, and hence, the skin surface, to which the preparation is applied, is not sticky and is smooth. Thus, the drawbacks of ointments, such as soiling of clothes and bad feeling, can be eliminated.

The creamy preparation of the present invention may optionally be incorporated with other active ingredients such as antihistaminics, analgesics, or the like.

The creamy preparation of the present invention and method for the preparation thereof are illustrated by the following Examples, but the present invention is not limited thereto. In the Examples, the purified water was prepared by purifying water with an ion exchange resin, and the viscosity was measured at 20° C. by a C-type viscosimeter (made by Tokyo Keiki Co., Ltd. Japan).

EXAMPLE 1

Dexamethasone acetate (25 mg) was dissolved in crotamiton (5 g) at about 70° C., and thereto were added isopropyl myristate (10 g), propylene glycol (10 g), polyoxyethylene sorbitan monolaurate (1 g), a 4% aqueous solution of a carboxyvinyl polymer (17 g), purified water (53 g) and a 1% aqueous solution of disodium edetate (1.2 g). The mixture was heated until about 70° to 80° C. on a water bath and thereto was added with stirring a 2% aqueous sodium hydroxide solution (2 g), and further, purified water was added thereto until the total amount became 100 g. The mixture was well stirred and then cooled to give a creamy preparation haing a viscosity of 60,000 centipoises and a pH of 4.30.

EXAMPLE 2

Fluocinonide (50 mg) was dissolved in crotamiton (7 g) with warming, and thereto were added liquid paraffin (10 g), propylene glycol (10 g), polyoxyethylene lauryl ether (1 g), a 4% aqueous solution of carboxyvinyl polymer (20 g), purified water (47 g) and a 1% aqueous solution of disodium edetate (1.2 g). The mixture was heated until about 70° to 80° C. on a water bath, and thereto was added with stirring a 2% aqueous solution of triethanolamine (4.68 g), and further purified water added thereto until the amount became 100 g. The mixture was stirred well and then cooled to give a creamy preparation having a viscosity of 65,000 centipoises and a pH of 4.47.

EXAMPLE 3

Prednisolone (500 mg) was dissolved in crotamiton (10 g) with warming, and thereto were added isopropyl myristate (10 g), propylene glycol (10 g), polyoxyethylene sorbitan monostearate (1.5 g), a 4% aqueous solution of carboxyvinyl polymer (17 g), purified water (48 g) and a 1% aqueous solution of disodium edetate (1.2 g). The mixture was heated until about 70° to 80° C. on a water bath and thereto was added with stirring a 2% aqueous solution of triethylamine 2.95 g), and further, purified water was added thereto until the total amount became 100 g. The mixture was stirred well and then cooled to give a creamy preparation having a viscosity of 54,000 centipoises and a pH of 4.65.

EXAMPLE 4

Dexamethasone (25 mg) was dissolved in propylene glycol (20 g) with warming, and thereto were added isopropyl myristate (10 g), polyoxyethylene sorbitan (1.0 g), a 4% aqueous solution of carboxyvinyl polymer (13 g), purified water (57 g) and a 1% aqueous solution of disodium edetate (1.2 g). The mixture was heated until about 70° to 80° C. on a water bath and thereto was added with stirring a 2% aqueous solution of triethanolamine (5.2 g), and further, purified water was added thereto until the total amount became 100 g. The mixture was stirred well and then cooled to give a creamy preparation having a viscosity of 43,000 centipoises and a pH of 4.80.

EXAMPLE 5

Hydrocortisone (500 mg) was dissolved in crotamiton (5 g) with warming, and thereto were added liquid paraffin (10 g), propylene glycol (10 g), polyoxyethylene lauryl ether (1.5 g), a 4% aqueous solution of carboxyvinyl polymer (27 g), purified water (38 g) and a 1% aqueous solution of disodium edetate (1.2 g). The mixture was heated until about 70° to 80° C. on a water bath, and thereto was added with stirring a 2% aqueous sodium hydroxide solution (10 g), and further purified water added thereto until the total amount became 100 g. The mixture was stirred well and then cooled to give a creamy preparation having a viscosity of 35,000 centipoises and a pH of 5.30.

EXAMPLE 6

Triamcinolone acetonide (100 mg) was dissolved in crotamiton (7 g) with warming, and thereto were added isopropyl myristate (10 g), propylene glycol (10 g), polyoxyethylene sorbitan monolaurate (1 g), a 4% aqueous solution of carboxyvinyl polymer (22 g), purified water (41 g) and a 1% aqueous solution of disodium edetate (1.2 g). The mixture was heated until about 70° to 80° C. on a water bath and thereto was added with stirring a 2% aqueous solution of triethylamine (6.5 g), and further, purified water was added thereto until the total amount became 100 g. The mixture was stirred well and then cooled to give a creamy preparation having a viscosity of 75,000 centipoises and a pH of 4.53.

What is claimed is:

1. A creamy preparation which comprises 0.001 to 9% by weight of a corticosteroid or ester thereof, a solvent consisting of 2 to 10% by weight of crotamiton and from 2 to less than 20% by weight of propylene glycol; 5 to 50% by weight of a fluid oily substance selected from the group consisting of a fatty alcohol having 8 to 18 carbon atoms, a monovalent or divalent fatty acid having 8 to 18 carbon atoms, an alkyl ester of a monovalent or divalent fatty acid having 8 to 18 carbon atoms in the fatty acid moiety and having 1 to 18 carbon atoms in the alkyl moiety, and a mixture thereof; 0.5 to 5% by weight of a nonionic surfactant; and an aqueous solution of 0.1 to 3% by weight of carboxyvinyl polymer; said preparation being regulated at a pH of 4 to 7 by neutralizing with a basic substance selected from the group consisting of an alkylamine having 1 to 4 carbon atoms, a dialkylamine having 1 to 4 carbon atoms in each alkyl moiety, a trialkylamine having 1 to 4 carbon atoms in each alkyl moiety, an alkanolamine having 1 to 4 carbon atoms in the alkanol moiety, a dialkanolamine having 1 to 4 carbon atoms in each alkanol moiety, a trialkanolamine having 1 to 4 carbon atoms in each alkanol moiety, trimethylolaminomethane, ammonia, and an aqueous solution of an alkali metal hydroxide and having a viscosity of 10,000 to 100,000 centipoises at 20° C., said amount of each component being based upon the total weight of the preparation.

2. A creamy preparation according to claim 1, wherein the solvent consists of 2 to 10% by weight of crotamiton and 5 to 10% by weight of propylene glycol based upon the total weight of the preparation.

3. A process for the preparation of a creamy preparation of a steroid compound, which comprises dissolving 0.001 to 1% by weight of a steroid compound selected from the group consisting of prednisolone, cortisone, triamcinolone, betamethasone, hydrocortisone, dexamethasone, methylprednisolone, fluocinolone, fluorometholone, triamcinolone acetonide, fluocinolone acetonide, fluocinonide, clobetasol 17-propionate, dexamethasone valerate, betamethasone valerate, betamethasone acetate, bethamethasone benzoate, flumethasone, prednisolone acetate, hydrocortisone valerate, betamethasone propionate, and bechlomethasone dipropionate in a solvent consisting of 2 to 10% by weight of crotamiton and 2 to less than 20% by weight of propylene glycol; adding thereto 5 to 50% by weight of a fluid oily substance selected from the group consisting of a fatty alcohol having 8 to 18 carbon atoms, a monovalent or divalent fatty acid having 8 to 18 carbon atoms, an alkyl ester of a monovalent or divalent fatty acid having 8 to 18 carbon atoms in the fatty acid moiety and having 1 to 18 carbon atoms in the alkyl moiety, and a mixture thereof, 0.5 to 5% by weight of a nonionic surfactant and a 1 to 10% aqueous solution of carboxyvinyl polymer, and then regulating at a pH of 4 to 7 by neutralizing with a basic substance selected from the group consisting of an alkylamine having 1 to 4 carbon atoms, a dialkylamine having 1 to 4 carbon atoms in each alkyl moiety, a trialkylamine having 1 to 4 carbon atoms in each alkyl moiety, an alkanolamine having 1 to 4 carbon atoms in the alkanol moiety, a dialkanolamine having 1 to 4 carbon atoms in each alkanol moiety, a trialkanolamine having 1 to 4 carbon atoms in each alkanol moiety, trimethylolaminomethane, ammonia, and an aqueous solution of an alkali metal hydroxide to give a creamy preparation having a pH of 4 to 7 and a viscosity of 10,000 to 100,000 centipoises at 20° C. and containing the carboxyvinyl polymer in an amount of 0.1 to 3.0% by weight based upon the total weight of the preparation.

4. A process according to claim 3, wherein the solvent consists of 2 to 10% by weight of crotamiton and 5 to 10% by weight of propylene glycol based upon the total weight of the preparation.

5. A creamy water and oil emulsion for treatment of inflamation of skin with a steroid having anti-inflammatory activity which is stable with change in ambient temperature, said emulsion having a pH of 4 to 7 and a viscosity of 10,000 to 100,000 centipoises at 20° C. and comprising as a dispersed phase said steroid dissolved in a solvent therefor which is a non-irritant of the skin, a nonionic surfactant, and a dispersed neutralized carboxyvinyl polymer gel and an oily material.

* * * * *